United States Patent [19]
Bruce et al.

[11] Patent Number: 5,387,515
[45] Date of Patent: Feb. 7, 1995

[54] PROCESS FOR PROVIDING A 6-KETONE FROM MORPHINE OR AN ETHER DERIVATIVE THEREOF USING MORPHINE DEHYDROGENASE

[75] Inventors: Neil C. Bruce, Cambridge; Lauren D. G. Stephens, Royston; Christopher R. Lowe, Saffron Walden, all of England

[73] Assignee: British Technology Group Limited, London, England

[21] Appl. No.: 183,307

[22] Filed: Jan. 19, 1994

Related U.S. Application Data

[63] Continuation of Ser. No. 784,445, Nov. 12, 1991, Pat. No. 5,298,414.

[30] Foreign Application Priority Data

May 12, 1989 [GB] United Kingdom ................ 8910958

[51] Int. Cl.6 .......................... C12P 17/18; C12P 7/26
[52] U.S. Cl. .................................... 435/148; 435/119
[58] Field of Search .............................. 435/148, 119

[56] References Cited

U.S. PATENT DOCUMENTS 4,204,044  5/1980  Suhara et al. ....................... 435/280
4,916,069  4/1990  Fujiwara et al. .................... 435/147
4,927,759  5/1990  Schofield et al. ................... 435/156

OTHER PUBLICATIONS

J. of Biol. Chem., vol. 260, No. 9, pp. 5265–5270, Yamano et al (1985).
R. Ammon et al, Chemical Abstracts, vol. 100 (3) No. 17087q (1984).
F. Crespi et al, Chemical Abstracts, vol. 110 (5) No. 33279r (1989).
J. A. Owen et al, Chemical Abstracts, vol. 99 (18) No. 151702a (1983).
D. A. Smith et al, Chemical Abstracts, vol. 85 (3) No. 13602c (1976).
P. Liras et al, Chemical Abstracts, vol. 84 (5) No. 27348r (1976).
V. Jhaveri. Chemical Abstracts, vol. 89 (3) No. 18999c (1978).

Primary Examiner—Douglas W. Robinson
Assistant Examiner—Jeffrey J. Sevigny
Attorney, Agent, or Firm—Nixon & Vanderhye

[57] ABSTRACT

Two enzymes, one an acetylmorphine carboxyesterase (AMCE), the other a morphine dehydrogenase (MDH), have been isolated from bacteria. The AMCE degrades heroin to morphine and the MDH oxidizes morphine to morphinone, with the aid of a cofactor. More particularly, the invention pertains to a process for preparing a 6-ketone from morphine or a methyl or ethyl derivative thereof. The process comprises oxidizing morphine or an ether derivative in the presence of a morphine dehydrogenase and the cofactor NADP+. These reactions are used in detection of heroin (using the two reactions coupled together) or morphine. The enzymes can be incorporated in sensors for this purpose.

2 Claims, 6 Drawing Sheets

PROCESS FOR PROVIDING A 6-KETONE FROM MORPHINE OR AN ETHER DERIVATIVE THEREOF USING MORPHINE DEHYDROGENASE

This is a continuation of application Ser. No. 07/784,445, filed Nov. 12, 1991, now U.S. Pat. No. 5,298,414.

BACKGROUND OF THE INVENTION

1. Field of the Invention

This invention relates to two new enzymes isolated from microorganisms, the microorganisms which produce these enzymes, the use of the enzymes in catalysing the degradation of heroin and a method and apparatus for the detection of heroin using these enzymes.

2. Description of the Prior Art

There is an urgent need for a method of detection of heroin in particulate form and in body fluids. In relation to particulate heroin, although many different analytical systems have been proposed, most are based on large pieces of equipment, such as mass spectrometry. In relation to body fluids, immunoassay has been used but this is better suited to laboratory testing where operatives with specialist skills are available. In principle, a cheaper and easier method for heroin detection could be provided if an enzyme specific for heroin was available and if the products of the enzymatic reaction could be detected using relatively simple instrumentation. Unfortunately, the range of enzyme activities presently available is rather limited and these enzymes do not possess the specificity required.

SUMMARY OF THE INVENTION

We have now found two enzymes which can be used in the detection of heroin (3,6-diacetylmorphine). One is an acetylmorphine carboxylesterase (hereinafter "AMCE") which catalyses the hydrolysis of heroin and has a high specificity for heroin. The other is a morphine dehydrogenase ("MDH") which has a high specificity for morphine, which is produced by hydrolysis of heroin. Either of these enzymes, or the two in combination, can be used to detect heroin, by reacting the enzyme with heroin or morphine obtained by its hydrolysis, and detecting the occurrence of an enzyme-catalysed reaction. One such method of detection of the reaction is electrical. In one electrical method, the reaction of heroin with the AMCE liberates acetate ions, which are detectable conductimetrically. The reaction of morphine with morphine dehydrogenase (MDH) requires a cofactor such as nicotinamide adenine dinucleotide phosphate (NADP+), which is reduced to NADPH concurrently with the oxidation of morphine to morphinone by the enzyme. This redox reaction can be used to generate an electric current at an electrode surface, particularly with the help of a redox mediator. Accordingly, the invention includes electrical sensors, especially of the conductimetric type for the AMCE alone and of the amperometric type for the AMCE and MDH enzymes together. These and other sensors, which can be of an optical, potentiometric, thermal or piezoelectric type, for example, for in the basis of convenient, portable sensors for detecting grains of heroin in the body fluids, luggage, clothing etc. of smugglers, traffickers and heroin users. Accordingly, this invention provides an important advance in the fight against and control of use of drugs.

The term "heroin" used throughout the specification comprises the free base and salts thereof, unless the context requires a more specific meaning.

In a first aspect, the invention provides the acetyl esterase enzyme. Since it catalyses the hydrolysis of heroin (3,6-diacetylmorphine), 3-acetylmorphine and 6-acetylmorphine, it is conveniently termed an acetyl morphine carboxylase (AMCE). It is thus distinguished from the commonly available porcine liver carboxylesterase which displays little or no activity towards the 6-acetyl group of heroin. The ability of the AMCE of the invention to act on the 6-acetyl group is an important distinguishing characteristic. Another distinctive feature of the AMCE is that it has a molecular weight of about 200,000 Daltons (as determined by elution from a gel filtration column calibrated with marker proteins). By the term "about" we mean to encompass variations which are usual in the determination of high molecular weights by this method and certainly to include a variation of up to 10%. Such a high native molecular weight of 200,000 is different from that of other acetyl carboxylesterases; those described for the nocardioform actinomycetes have molecular weights of 84,000 and 39,000, respectively (E. F. Eubanks et al., J. Bacteriology 120, 1133–1143, 1974), while the acetyl carboxylesterases described in Bacillus subtilis have molecular weights of 160,000 and 31,000, respectively (J. B. Higerd and J. Spizizen, J. Bacteriology 114 1184–1192 1977). The mammalian carboxylesterases have molecular weights in the region of 165,000 (K. Kirsch, "Carboxylic ester hydrolase" in "The Enzymes" ed. P. D. Boyer, Vol. 5, Academic Press Inc. New York, 1971, pages 43–69.

The AMCE of the invention is highly active at alkaline pH and over a wide pH range, whereas other microbial acetyl carboxylesterases exhibit a bell-shaped pH-activity profile at generally lower pHs. Thus the AMCE shows significant activity at pHs from 8 or below to 10 or above.

Example 1 hereinafter describes Other features of the AMCE, but it is expected that it will be possible to vary some of these by changing the conditions of growth of the microorganism which produces it OF by a higher degree of purification of the enzyme. Accordingly, it is preferred not to rely on such characteristics as the faster rate of reaction with 3-acetylmorphine than with 6-acetylmorphine or the rate of thermal deactivation, in the most general definition of the enzyme. Any one or more of them can be considered (as the context permits) as alternative ways of defining the enzyme, but they are best seen as one or more preferred, additional characteristics to one or more of those defined above.

The AMCE is obtainable from a bacterial strain isolated from nature. This strain is of the genus Rhodococcus, and is referred to herein simply as "Rhodococcus H1". It has been deposited as a patent deposit under the Budapest Treaty on the International Recognition of Deposits of Microorganisms for the Purposes of Patent Procedure, on 7th Mar. 1989 at the National Collections of Industrial and Marine Bacteria (NCIMB), 23 St. Machar Drive, Aberdeen AB2 1RY, Scotland, under deposit number NCIMB 40120 This bacterium, together with mutants and variants which produce the AMCE of the invention, is part of the present invention. It can be produced by culturing such a bacterium on a source of carbon and nitrogen, the preferred carbon source comprising heroin, disrupting the cells, and recovering the enzyme from the disrupted cells. The organism will grow on glucose as sole carbon source, but produces lower AMCE activity in the cells.

In a second aspect, the invention provides a morphine dehydrogenase (MDH) enzyme. The MDH of the invention can be defined in several different ways, but is probably best defined by its partial amino acid sequence shown as SEQUENCE ID NO. 1 in the sequence listing section at the end of the description, immediately before the claims. The protein sequence databases PIR and DOOLITTLE were searched with a FASTP program and failed to reveal any significant sequence homology.

MDH of the invention, are included in the present invention. The *P. putida* M10 converts heroin to morphine and morphine to morphinone, producing an acetyl carboxylesterase to carry out the first stage and the MDH to carry out the second stage. Since the *P. putida* M10 produces an acetyl carboxylesterase of very low activity, it is not of much interest for use in a heroin sensor. Rather, according to a very important and valuable feature of the invention the AMCE is coupled with the MDH for the detection of heroin, according to the reaction scheme:

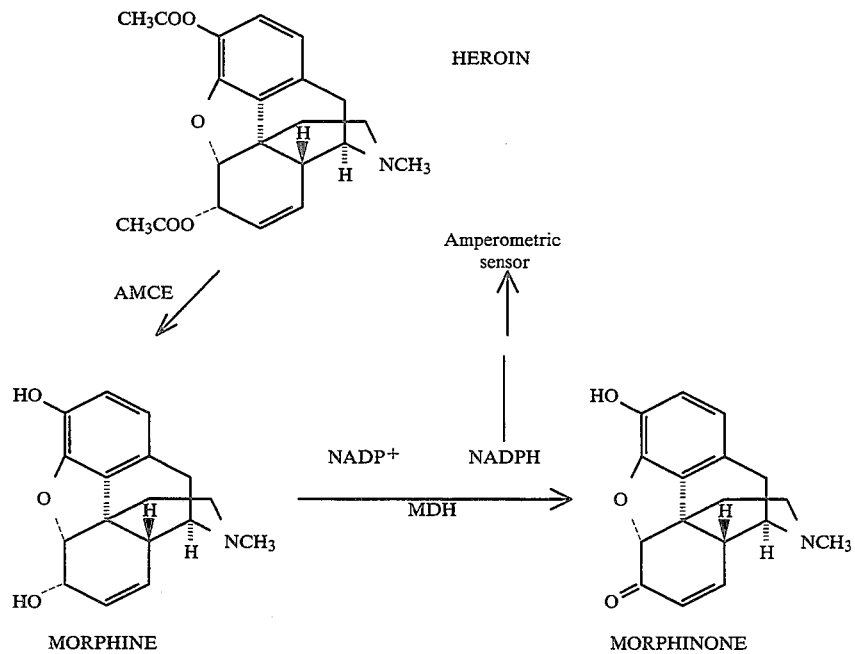

Alternatively or additionally the MDH of the invention can be characterised by any of the following properties. With the aid of a cofactor, notably $NADP^+$, it oxidises morphine to morphinone. It oxidises codeine and ethylmorphine. It has no significant enzymatic activity on heroin or many other alkaloids of similar ring structure. Its molecular weight, measured in the same way as for the AMCE, is about 32,000 Daltons. The optimal activity of the enzyme is exhibited at a high pH, initially estimated to be about 10, but now fixed more precisely as at about 9.5, in glycine-sodium hydroxide buffer.

Examples 2 to 4 hereinafter describe other features of the MDH, but it is expected that it will be possible to vary some of those by changing the conditions of growth of the microorganism which produces it or by recombinant DNA technology, which can be used to produce the enzyme. Accordingly, it is preferred not to rely on such characteristics in the most general definition of the enzyme. Any one or more of them can be considered (as the context permits) as alternative parameters for use in defining the enzyme, particularly the isoelectric point of 4.2 (see Example 4), but they are best seen as one or more preferred, additional characteristics to one or more of those defined above.

The MDH is obtainable from a strain of the bacterium *Pseudomonas putida* isolated from nature, herein designated "M10". A Budapest Treaty patent deposit of this bacterium has been made at the NCIMB, on 7th Mar. 1989, under the number NCIMB 40119. This bacterium, together with mutants and variants producing the For the first time it is possible to oxidise morphine or a 3-(lower alkyl) ether thereof, the lower alkyl group having 1 to 4 carbon atoms, enzymically, in the presence of the MDH and a cofactor such as described above. Preferably the oxidation is carried out in air and at 25° to 35° C. The reaction products, notably morphinone and codeinone, are useful as analgesics.

DESCRIPTION OF THE PREFERRED EMBODIMENTS

Figure 1:
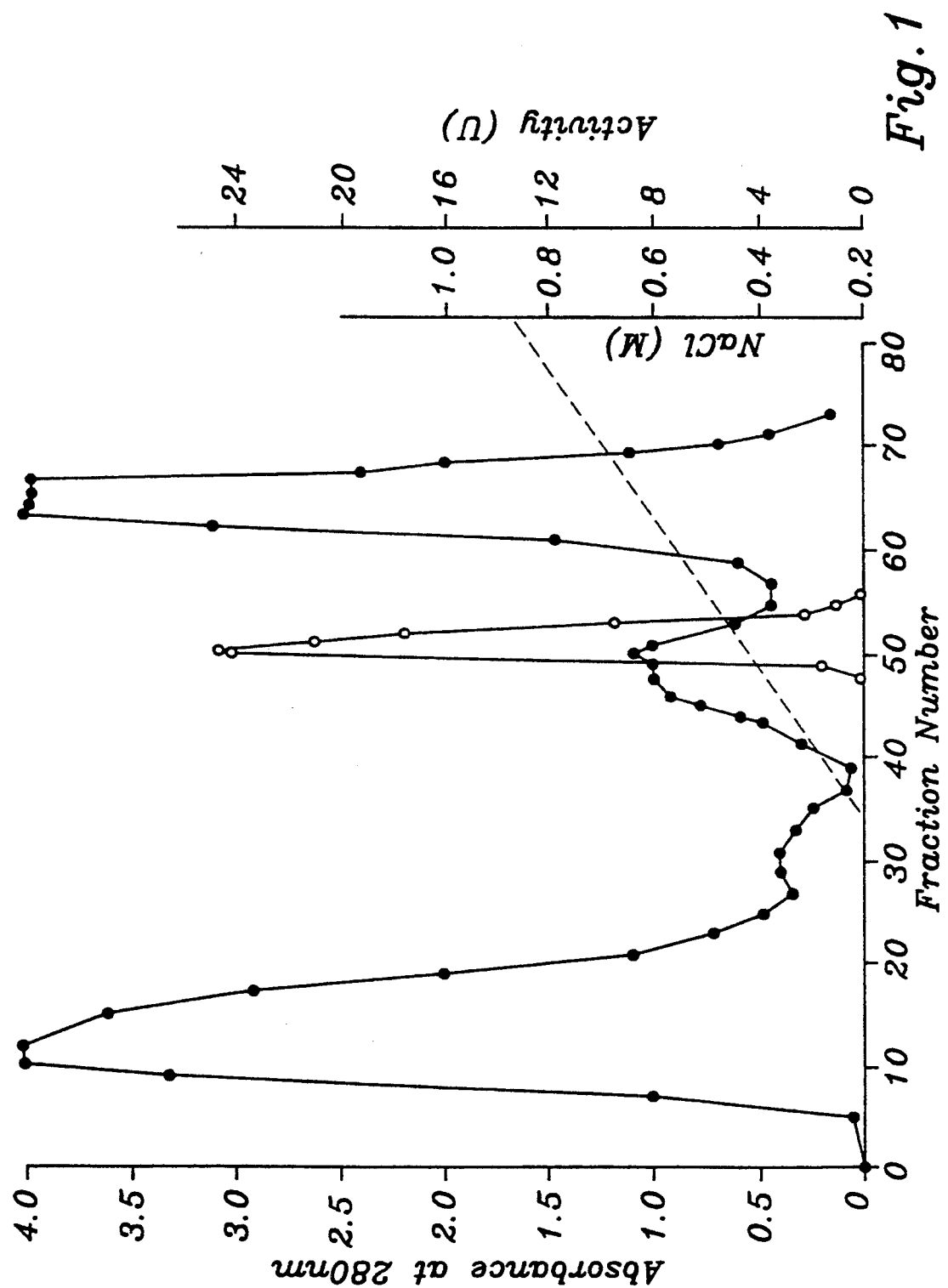
FIG. 1 plots the course of an important stage in the chromatographic purification of the AMCE (see Example 1)

Both the enzymes of the invention can be produced by culturing the respective microorganisms on a source of carbon and nitrogen. Any conventional sources can be used, but it is preferred to grow the Rhodococcus H1 on a carbon source comprising heroin and the *P. putida* M10 on a carbon source comprising heroin or morphine. The Rhodococcus H1 grows on glucose as carbon source but the AMCE activity of the cells is lower than when it is grown on heroin. The MDH is produced constitutively and therefore the *P. putida* M10 can be cultured on glucose to produce a highly active preparation of MDH. For both microorganisms cultivation is preferably aerobic. Any usual temperature, e.g. within the 20° to 40° C. range, preferably 25° to 35° C., can be used. To obtain the enzyme the cells can be disrupted in any conventional way. Preferably a cell-free extract is made. The enzyme is then recovered from the cells or extract.

Instead of the precise starting organism deposited, a mutant thereof, e.g. derived by gamma-ray irradiation or use of a chemical mutant, induction by culture on another medium etc. or a transconjugant thereof with another bacterium or an artificially produced variant can be used.

The enzyme or some modification thereof can also be made by recombinant DNA technology using methods well recognised in that art. These may entail producing the enzyme in another host organism.

The enzymes of the present invention are useful primarily in the detection of heroin. The preferred method involves use of both enzymes together, the AMCE to degrade the heroin to morphine and the MDH to oxidise the morphine, the latter reaction requiring a cofactor. Alternatively, the AMCE can be used on its own. Also the MDH-cofactor system can be used on its own for detection of morphine.

The invention is particularly applicable to the detection of grains of powdered heroin or morphine (free base or any of their salts). Samples containing the drug can be collected from luggage, cargo or about the person by blowing air over the affected area, collecting the air and concentrating the particles contained in it. A suitable apparatus is shown schematically in FIG. 6. In order to remove drug particles 1 which have become electrostatically held to plastic surfaces in the luggage 2, the air can first be passed through a neutraliser unit 3 which generates positively and negatively charged ions. These can be generated in any conventional way, e.g. by a $^{210}Po$ radioactive source (not shown). The ionised air is then sent under pressure through a conduit 4 into the luggage 2. The drug particles held on the plastic surfaces within the luggage are thereby electrically neutralised. Air is exhausted from the luggage by gentle suction through conduit 5, entraining the drug particles 1. These drug particles in the withdrawn air are focussed and concentrated. This can be done by conferring a negative charge on the particles with the aid of an air ioniser 6 and collecting them on an earthed electrode, 7 of a biosensor. Instead of the ioniser 6 and electrode 7, the particles could be collected on an ultrafine sieve, or within a porous plug of, say, cotton wool, depending on the intended method of detection.

The invention is also applicable to the detection of heroin or morphine in biological fluids, especially in urine and blood. Heroin is hydrolysed in vivo to morphine and therefore use of the MDH is appropriate for such detection.

The hydrolysis of heroin by the AMCE must take place in an aqueous medium. The enzyme or the sample or both should be in an aqueous medium immediately before contact. The aqueous medium is used to solubilise the heroin (as acid addition salt) and to allow enzyme activity. For detection of solid particles it is often convenient to introduce the enzyme into a humectant composition. Thus, for example where a biosensor is used for the detection of solid particles, the sampling surface of the biosensor is pre-coated with the enzyme(s) in a humectant composition. Similarly where a test strip is used, the strip support is coated with a humectant composition containing the enzyme. A humectant is desirable in order to prevent the enzyme from dehydration caused by the air flow from the sample apparatus.

The method of detection may depend on conductance, e.g. to detect acetate ions liberated from the hydrolysis of heroin. In that event, the humectant should be one which provides a stable initial level of conductance (blank reading) to be attained, which is not badly affected by changes in relative humidity in the surrounding atmosphere which might occur during sampling. It should thus allow the biosensor to be used in the variety of climatic conditions encountered in different countries.

For the conductimetric method, a simple, inexpensive humectant such as glycerol with sodium chloride, suitably buffered, is adequate. Preferably the buffer is imidazole. The composition desirably contains (by weight) from 70 to 90% glycerol, 2 to 3% sodium chloride and 17 to 7% of aqueous imidazole of concentration appropriate to the pH required, e.g. 2 millimolar for pH 7.5. Particularly preferred is a composition comprising (by weight), about 10% of 2 mM aqueous imidazole, about 87.5% glycerol and about 2.5% sodium chloride.

For other detection procedures, other humectants and buffers can be used. Thus, in an amperometric method, 50 mM glycine/sodium hydroxide, pH 10 can be substituted for imidazole. Alternatively, polyvinyl pyrrolidone, buffer and sodium chloride can be used.

The principle of operation of a conductimetric biosensor involves the application of an electric field across a pair of electrodes in an electrolyte. The electric field can be generated by application of a sinusoidal voltage wave form across the electrodes in order to minimise or eliminate undesirable Faradaic processes, double-layer charging and concentration polarisation at the surface of the electrode. In order to detect accurately the small conductance generated by acetate ions it is necessary to introduce comparator circuitry. Preferably an Owen type bridge circuit as described in Example 5 is used. Of course, the acetate ions do not have to be detected conductimetrically.

Figure 4:
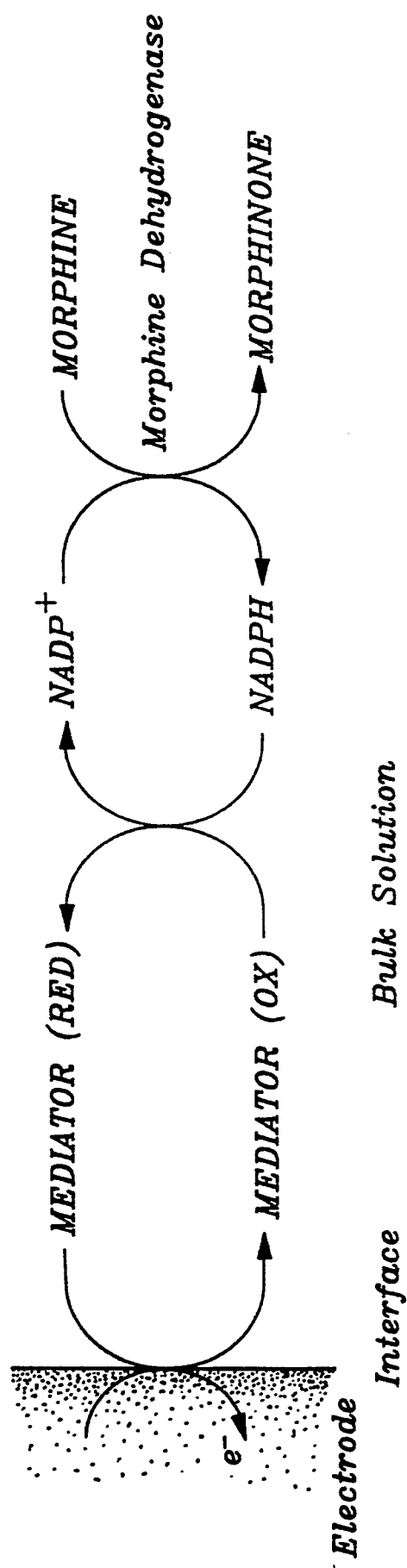
FIG. 4 shows schematically the mediated transfer of electrons from the morphine to morphinone oxidation reaction to an electrode (see Example 7)
Figure 5:
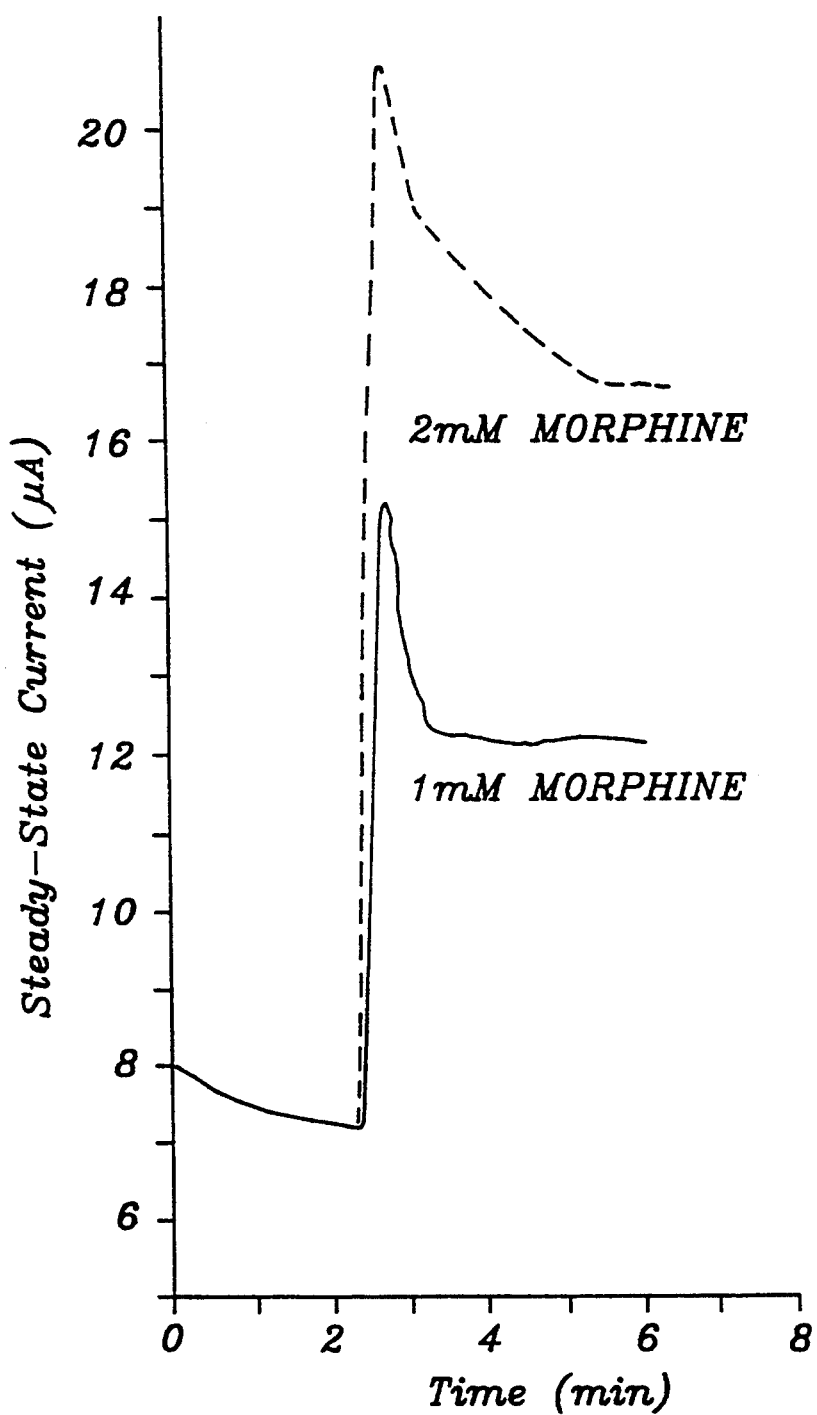
FIG. 5 is a graph of steady state current response against time at various concentrations of morphine in an amperometric sensor for morphine using MDH (see Example 7)

More preferably, the morphine liberated by the hydrolysis is detected. Especially, both enzymes are employed and the heroin is then detected amperometrically. Amperometric detection depends on using the oxidation of morphine to morphinone via the concomitant reduction of the cofactor, especially $NADP^+$ to NADPH, electrochemically to transfer electrons to an electrode and thereafter to an external electrical circuit. One method of transfer is via a mediator, as illustrated in FIG. 4 of the drawings. Many mediators are well Known for this general type of reaction in which the cofactor for the enzyme is re-oxidised and most of these are operable in the present instance. Examples are hexacyanoferrate ions, phenazine methosulphate or ethosulphate, ferrocene/diaphorase or 4-methylquinone. Any of the usual electrochemical cell arrangements for the transfer of electrons from a chemical reaction to an electrode can be used. The cofactor can be NADP+ or any operable analogue thereof such as 3-acetylpyridine ADP. NAD+ and nicotinamide hypoxanthine diphosphate have not been found to be operable under conditions tried to date.

A preferred composition for use in detecting heroin therefore comprises (1) the AMCE, (2) MDH and (3) a cofactor for the MDH, especially NADP+. Optionally, depending on the method of detection, the composition can also include a humectant or a mediator.

Although in the two-enzyme method, the best heroin-degrading acetyl carboxylesterase is believed to be that of the invention, it is possible in principle to use other such acetyl carboxylesterases. Clearly such an acetyl carboxyesterase is present in the *Pseudomonas putida* strain "M10" since this bacterium is able to produce morphine from heroin, but its activity appears to be low.

The invention includes specifically an amperometric biosensor comprising a working electrode, a reference electrode and a counter-electrode in contact with an electrolyte containing the MDH, a cofactor therefor and (usually) a mediator. Where the current is small, the counter-electrode can also serve as the reference electrode. It also includes a conductimetric biosensor comprising a pair of electrodes in contact with an electrolyte containing the AMCE. The electrodes of the biosensor and the external circuitry are those appropriate to conductimetric or amperometric detection of current, as the case may be.

The MDH reaction is also detectable spectrophotometrically in various ways. According to one aspect, the oxidation of morphine is used to drive a redox reaction in which a colour change or a change in UV absorption occurs. Thus, the cofactor itself can be used to detect the reaction by observing the reduction of NADP+ to NADPH, particularly as an increase in absorbance at about 340 nm. Alternatively, the redox reaction of the cofactor can be used to drive a redox reaction or a "system" comprising more than one such reaction, in which a colour change takes place. For example, using phenazine methosulphate as a mediator, nitroblue tetrazolium can be reduced to a formazan, giving a blue-purple colour. Instead of nitroblue tetrazolium, triphenyl tetrazolium chloride, iodonitro tetrazolium chloride, neotetrazolium chloride or 2,6-dichlorophenolindophenol could be used.

In other sensors of the invention an optical transducer (e.g. an optical fibre) or a thermal transducer (e.g. a thermistor), or a potentiometric or piezoelectric transducer is put into a working relationship with the enzyme.

The following Examples illustrate the invention. "Sephadex", "Sephacel" and "Mimetic" are Registered Trade Marks in many countries.

EXAMPLE 1

Preparation of an Acetylmorphine Carboxylesterase (AMCE) from the Bacterial Strain "Rhodococcus H1"

MATERIALS AND METHODS

Microorganisms

The organism Rhodococcus H1 was isolated from Cambridge garden soil by enrichment with heroin as the sole carbon source.

Cultures of Rhodococcus H1 were grown in 250 ml Ehrlenmeyer flasks containing 50 ml. of defined minimal medium consisting of $(NH_4)_2SO_4$ (0.5 g.), $K_2PHO_4$ (2.0 g.), $KH_2PHO_4$ (0.2 g.) and $Mg\,SO_4$ (0.05 g.) per liter containing trace elements as described by J. A. Barnet and M. Ingram, Journal of Applied Bacteriology, 18, 131–148 (1955), supplemented with 5 mM glucose and 5 mM heroin. (Note: the bacteria will give lower yields of biomass but a higher specific activity of AMCE when grown solely on 10 mM heroin). After 48 hours of growth at 30° C. in a shaking incubator (180 rev/min), the contents of the flask were poured aseptically Into a 2 liter Ehrlenmeyer flask containing 750 ml of the same medium. The cultures were incubated for 48 h. For bulk preparation of bacteria, the contents of a 2 liter flask were used as inoculum for a 10 liter culture vessel, containing 9.25 liters of sterile medium. The bulk cultures were incubated at 30° C., with forced aeration for 48 h or until 80–85% of the carbon source had been utilised.

Cell-free extracts were prepared by resuspending cell paste at a concentration of 0.5 g/ml in buffer A (50 mM potassium phosphate buffer mixture, pH 7.0, 1 mM dithiothreitol). The cell suspension was kept chilled in a crushed ice bath and sonicated for periods of 15 seconds. in a Soniprep 150 MSE Ultrasonic Disintegrator at an amplitude of 10 μm, peak to peak, for a total sonication time of 3 min. The bacterial extracts were centrifuged at 30,000g for 15 min in a Sorval RC-5C centrifuge, using an 8×50 rotor at 4° C. to remove the unbroken cells and debris.

Chemicals

3-Acetyl- and 6-acetylmorphine were prepared from morphine and heroin, respectively according to the methods of L. E. Welsh, J. Org. Chem. 19, 1409–1415 (1954) and C. I. Wright, J. Pharmacol. Exp. Therap. 71. 164–168 (1941) respectively. Other chemicals are commercially available or readily preparable by known methods.

Enzyme Assays

Esterase activity was assayed by two spectrophotometric methods. In the first assay, phenyl acetate was used as the substrate. The reaction was maintained at 30° C. and the formation of phenol monitored by UV absorbance at 275 nm. The reaction mixture contained, in a total volume of 2 ml, 50 mM Tris-HCl buffer mixture, pH 7.5, 4 mM phenyl acetate and enzyme. The second spectrophotometric method to monitor esterase activity used the pH indicator dye bromocresol purple, since enzymic hydrolysis of diacetylmorphine rapidly lowered the pH of a poorly buffered assay mixture. Bromocresol purple (0.1 g) was dissolved in 16ml of 0.01N NaOH solution and made up to 250 ml with distilled water. The change in absorbance at 588 nm was measured as the rate of reaction. The reaction mixture contained in a total volume of 1 ml; 2 mM imadazole buffer, pH 7.0, 2 mM diacetylmorphine, 10 μl bromocresol purple solution and enzyme. A third enzyme assay depended upon the separation of diacetylmorphine, 6-acetylmorphine and morphine by HPLC. The solvent system was that described by J. G. Umans, Journal of Chromatography 233, 213–225 (1982). The reaction mixture contained 1 mM heroin and enzyme in 2 ml of 50 mM Tris-HCl buffer mixture, pH 7.5. From the assay mixture, incubated at 30° C., in a shaking water bath, 200 μl aliquots were removed at intervals and the reaction stopped by the addition of 5 μl of concentrated acetic acid and the protein precipitate removed by centrifugation in a Microfuge, before samples (50 μl) of the supernatant were analysed by HPLC.

The unit of enzyme activity is defined as the amount of enzyme necessary to hydrolyse 1 μmol of phenyl acetate into phenol in 1 min.

Protein In extracts used in enzyme assays was measured by the method of M. M. Bradford, Analytical Biochemistry 72, 243–254 (1976).

Purification of the AMCE

Crude extracts was prepared from 19 g (wet weight) of frozen diacetylmorphine-grown cells that were thawed at 4° C. before extraction. Cells were resuspended in buffer A. The cell suspension was kept chilled in a crushed ice bath and sonicated for periods of 15 s in a Soniprep MSE Ultrasonic Disintegrator at a amplitude of 10 μm peak to peak for a total sonication time of 3 min. The bacterial extracts were centrifuged at 30,000g for 15 min in a Sorval RC-5C centrifuge, using an 8×50 rotor at 4° C. to remove the unbroken cells and debris.

1. Streptomycin sulphate

A neutralised 10% (w/v) streptomycin sulphate solution was added dropwise with constant stirring to 33 ml of crude extract until 0.1 ml of streptomycin sulphate had been added per 1 ml of cell extract. After stirring at 4° C. for 5 min, the nucleic acid percipitate was removed by centrifugation.

2. DEAE-Sephacel ion-exchange chromatography

The streptomycin-treated preparation was applied to a DEAE-Sephacel column (2.5×30 cm) that had previously been equilibrated with buffer A. After adsorption on to the column, the sample was washed extensively with buffer containing 0.1M NaCl until no further absorbance at 280 nm was detected in the eluant thus purifying it from much contaminating protein. The AMCE was eluted with 400 ml of buffer A in a linear gradient running from 0.1M–1.0M NaCl. Fractions of 8 ml were collected at a flow rate of 18 ml/h. The enzyme eluted at approximately 0.25M NaCl. The course of the chromatography is shown In FIG. 1 in which the esterase activity is denoted by open circles and the protein content by filled circles. The peak of esterase activity occurred at fractions 50–56 within a relatively small protein content peak.

3. Sephadex G-150 gel filtration

Figure 2:
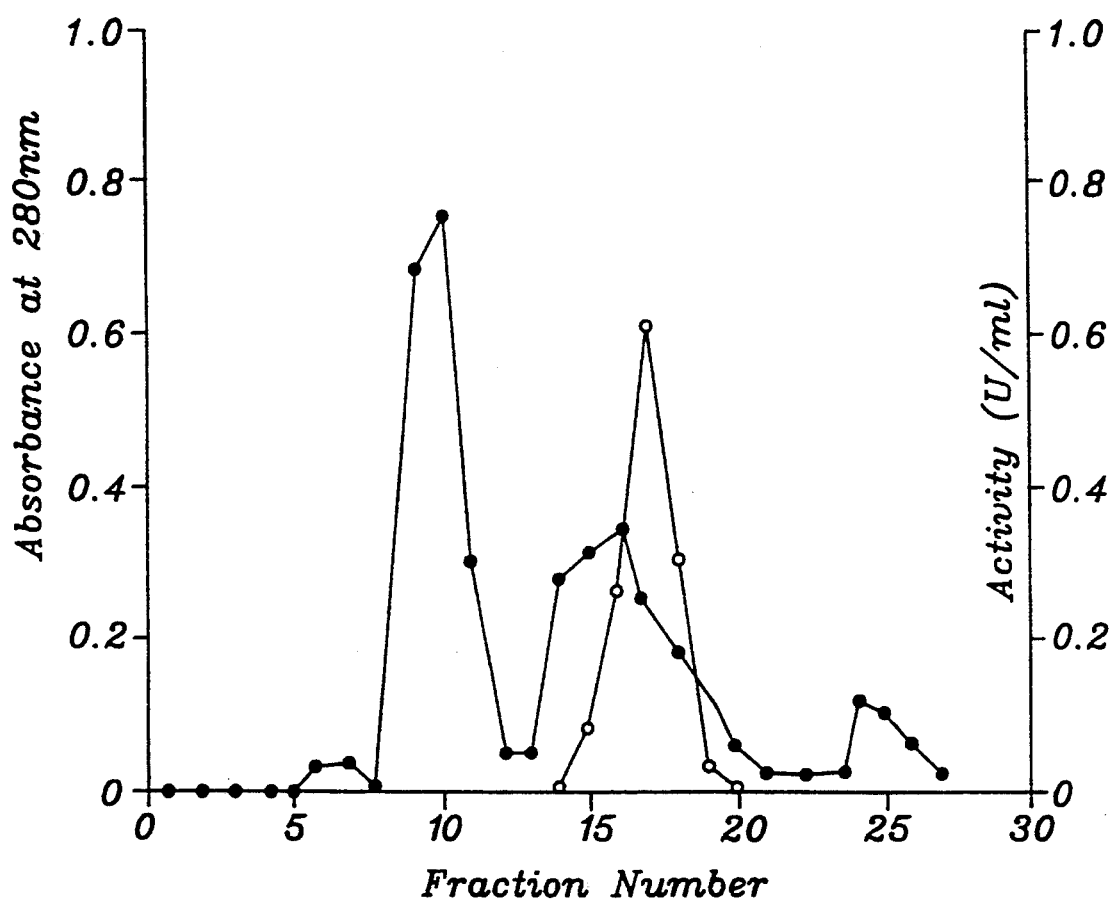
FIG. 2 plots the course of a further stage in the chromatographic purification of the AMCE (again, see Example 1)

Fractions from the ion-exchange column containing the highest esterase activity were combined and concentrated to 5 ml by ultrafiltration. The concentrate was then applied to a Sephadex G-150 column (1.5×75 cm) that had previously been equilibrated with buffer B (50 mM MOPS, pH 7.5). The flow rate was maintained at 10 ml/h and fractions of 6 ml were collected. The course of the chromatography is shown in FIG. 2, in which the esterase activity is denoted by open circles and protein content by solid circles. The peak of esterase activity occurred at fractions 14–19, within a second, broad protein content peak.

4. FPLC Mono O chromatography

Fractions from the Sephadex G-150 column containing the highest esterase activity were loaded on to the mono Q HR 5/5 column (Pharmacia). The column had previously been equilibrated with buffer B. The column was washed with buffer B until no further absorbance at 280 nm was detected, then the enzyme was eluted with 20 ml of buffer B in a linear gradient running from 0–1M NaCl. Fractions of 1 ml were collected at a flow rate of 1 ml/min.

Polyacrylamide Electrophoresis (PAGE)

PAGE was performed by the method of U. K. Laemmli, Nature 227, 680–682 (1970) on a 1 mm thickness vertical slab gel (Bio-Rad), containing 11% (w/w) acrylamide in the resolving gel. Protein was detected by staining the gel for 3 h with Coomassie Brilliant Blue R250 dissolved in a solvent system consisting of methanol-water-acetic acid (4:5:1 by vol). Gels were diffusion-destained by repeatedly washing them in the above solvent mixture, and allowing the stain to diffuse out in solution in the solvent.

RESULTS

Growth of the isolate Rhodococcus H1 with heroin as the sole carbon source produced an AMCE of specific activity (expressed in units/mg protein), some 15-fold greater than that observed with growth on glucose.

The enzyme was highly purified to electrophoretic homogeneity (over 200 fold in terms of specific activity), by the procedure described. Steps 1–3 achieved an approximately 15-fold purification, step 4 (the Mono-Q chromatography) a further 18-fold. The enzyme was homogeneous when subject to PAGE.

pH Optimum

The AMCE has a broad pH optimum range from 7.0 to 9.5 in Tris-HCl buffer, using phenyl acetate substrate. This plateau-like pH activity relationship ensures that the AMCE can be used at a high pH, e.g. of 9.5 to 10, which is a particular advantage in the combined use of AMCE and MDH. Potassium phosphate buffer appears to have an inhibitory effect on esterase activity.

Effect of Temperature

The enzyme (60 μg) was incubated at 40° C. in 50 mM potassium phosphate buffer, pH 7.0 and its activity plotted against time. From the graph it was deduced that it had a half-life of 14 min at 40° C.

Substrate Specificity of the AMCE

A comparison of AMCE activities with 3-acetyl- and 6-acetylmorphine was examined with each compound at a concentration of 1.0 mM in a reaction mixture containing 3 ml potassium phosphate buffer, pH 7.5 and purified enzyme (5U). The reaction mixture was incubated in a shaking water bath at 30° C. and 200 μl samples were removed at intervals and the reaction stopped by the addition of 5 μl of concentrated acetic acid. The samples were then centrifuged to remove any precipitated protein. Aliquots of 50 μl were analysed by HPLC. The acetyl esterase rapidly hydrolysed 3-acetylmorphine to morphine. 6-Acetylmorphine was also a substrate for the AMCE, but the rate of hydrolysis was much slower than that for the 3-acetyl analogue. Thus, the time taken to reduce the substrate concentration by 20% was 2 minutes for 3-acetylmorphine and 4 hours for 6-acetylmorphine.

Molecular Weight

The molecular weight of the native enzyme was determined by the method of Andrews, Biochem. J. 91, 222–233 (1964) from measurements on a column of Sephacryl S-200 (1.5×75 cm) calibrated with marker proteins. After the column was equilibrated with 20 mM Tris-HCl, pH 7.5, a solution containing purified enzyme was applied to the bed surface and eluted with equilibration buffer at a flow of 4 ml/h, collecting 1.5 ml fractions. The elution volume of the AMCE corresponded to a molecular weight of 200,000.

EXAMPLE 2

Isolation of a Morphine Dehydrogenase (MDH) from *Pseudomonas putida* M10

MATERIALS AND METHODS

Microorganisms

The starting microorganism, M10 was isolated from industrial waste liquor by enrichment with heroin. For reference purposes, other Pseudomonas bacteria were studied. These were: *P. putida* ATCC 17464, *P. testosteroni* ATCC 17454 and *P. fluorescens*, NCIMB 9815, and *P. aeruginosa* strain K ATCC 25102, kindly supplied by Judith Greenwood, Department of Biochemistry, University of Cambridge, England.

Cultures of *P. putida* M10 were grown and cell-free extracts were prepared as for Rhodococcus H1 in Example 1.

Chemicals

3-Acetyl- and 6-acetylmorphine were prepared from morphine and heroin respectively, according to the methods of L. E. Welsh, J. Org. Chem. 19, 1409–1415 (1954) and C. I. Wright, J. Pharmacol. Exp. Therap. 71, 164–168 (1941) respectively. Other chemicals are commercially available.

The resolution and identification of 3-acetyl-, 6-acetylmorphine, morphine, heroin, codeine and codeinone was determined by HPLC analysis at 218 mm, on Waters 450 system linked to an Waters 740 Data Module. The 25 cm length column contained 5$\mu$ Spherisorb-ODS (C-18) reverse-phase packing. The solvent system was that described by J. G. Umans, Journal of Chromatography 233,213–225 (1982).

Enzyme Assays

MDH was measured by ultra-violet spectroscopy by following the reduction of $NADP^+$ at 340 mm in 50 mM glycine-NaOH buffer, pH 10, containing 2 mM morphine or codeine, 2 mM $NADP^+$ and enzyme in a final volume of 1 ml. The unit of enzyme activity is defined as the amount of enzyme necessary to reduce 1 $\mu$mol of $NADP^+$ per minute.

Protein in extracts used in enzyme assays was measured by the method of M. M. Bradford Analytical Biochemistry 72, 248–254 (1976).

Purification of the MDH

Figure 3:
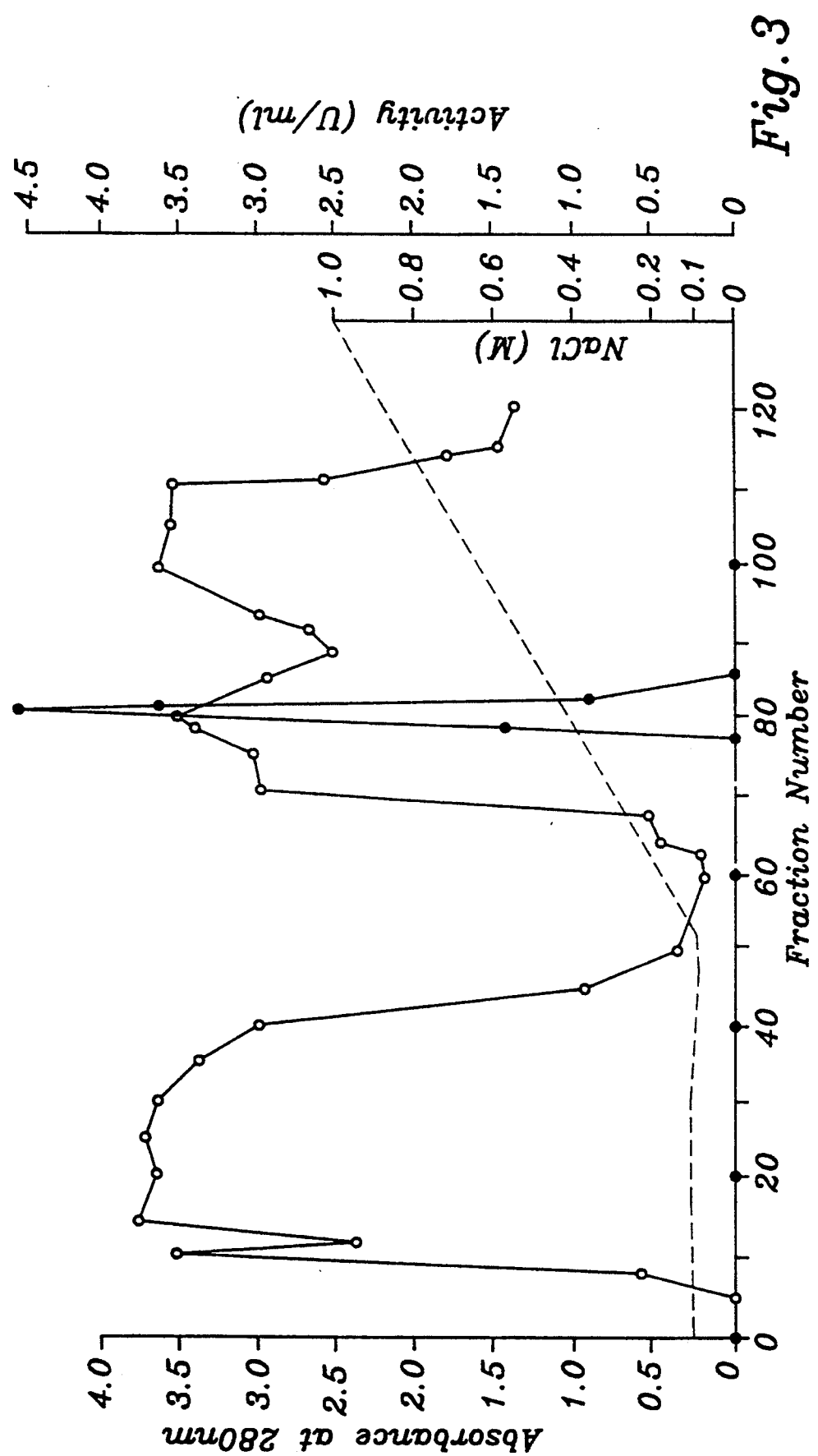
FIG. 3 plots the course of an important stage in a chromatographic purification of the MDH (see Example 2)

1. Streptomycin sulphate: As in Example 1.
2. DEAE-Sephacel ion exchange chromatography: as in Example 1. The course of this chromatography is shown in FIG. 3 of the drawings in which the open circles denote protein and the filled in circles represent MDH activity in Units/ml. Enzyme activity was eluted at 0.37M NaCl on the linear salt gradient.
3. Sephacryl S-300 gel filtration: as for the Sephadex G-150 filtration in Example 1. Fractions 28–60 contained protein, peaks being obtained at around fractions 32 and 42. Fractions 35–55 showed MDH activity, with a peak at around fraction 44.

RESULTS

All the pseudomonads screened possessed the ability to grow at the expense of heroin; however, only *P. putida* M10 degraded morphine and codeine when they were supplied as the sole carbon source. Furthermore, during the metabolism of these compounds, the medium became progressively darker. Heroin metabolism by washed cells of *P. putida* M10 grown at the expense of heroin was tested directly by measuring the disappearance of substrates from incubation mixtures by HPLC. Cells grown on heroin readily metabolised morphine, codeine and ethylmorphine. Thebaine, however, was not degraded at all. No degradation of the morphine alkaloids was detected when *P. putida* M10 was grown at the expense of glucose.

The Initial Step in the Metabolism of Diacetylmorphine

By HPLC analysis and reference to authentic standard compounds, both the acetyl ester groups of heroin were shown to be hydrolysed by whole washed cells of *P. putida* M10 grown at the expense of heroin. Further experiments with cell extracts showed that an esterase enzyme hydrolysed heroin to 6-acetylmorphine, then catalysed further hydrolysis to morphine. No traces of 3-acetylmorphine were found to accumulate. When cell free extract was replaced in the reaction mixture by boiled cell extract, only slow hydrolysis of heroin to 6-acetylmorphine occurred. Each strain of pseudomonad was screened for acetyl carboxy esterase activity after growth with heroin. In each case, growth with the alkaloid substrate led to enhanced esterase activities compared with those found in extracts of glucose-grown cells.

Further Metabolism of Morphine

Crude extracts from cells of *P. putida* M10 grown with diacetylmorphine as the growth substrate, did not show any activity against either morphine or codeine, even when high concentrations of crude extract protein were used. The extracts showed an absolute requirement for $NADP^+$; $NAD^+$ was shown not to be a substrate. Activity was not observed when crude extract was replaced with boiled extract in the reaction mixture.

The MDH was found to be purified 100 fold (in terms of its specific activity in units/mg protein) by anion exchange chromatography on DEAE-Sephacel followed by gel filtration chromatography on Sephacryl S-300 (FIG. 3). Although the enzyme was not found to be electrophoretically homogeneous, morphinone was not further degraded, thus indicating that the other enzymes of the morphine degradation pathway had been removed.

pH Optimum

The effect of pH on enzyme activity over the pH range 7 to 11 showed an optimum activity towards morphine at pH 10 in glycine-NaOH buffer mixture.

The specific activity was reduced at pH values above 10.5. The more highly purified material prepared in Example 4 showed optimum activity at pH 9.5.

Induction of the Novel Dehydrogenase Enzyme in Pseudomonads

*P. putida* M10 and the reference pseudomonads were screened for $NADP^+$-dependent MDH activity. The cells were grown on (a) heroin (10 mM), (b) morphine (5 mM), supplemented with glucose (5 mM) or (c) glucose (10 mM) each "M10" showed MDH activities of 0.65, 0.02 and 0.39 respectively, whereas all the other pseudomonads showed nil MDH activity in all cases.

Identification of the Primary Reaction Product of Morphine and Codeine Degradation In order to resolve the degradation product of morphine or codeine metabolism by *P. putida* M10, the alkaloid (100 μmol) in 50 ml 25 mM glycine-NaOH buffer, pH 10.0 was incubated for 3 h at 30° C. with highly purified enzyme (4U). At intervals during the incubation, 300 μl aliquots were removed from the reaction mixture and the reaction stopped by the addition 5 μl of concentrated acetic acid. The samples were then centrifuged to pellet any precipitated protein and 50 μl of supernatant was analysed by HPLC. The enzymic degradation product of codeine was identified as codeinone by reference to authentic standard compounds. In order to confirm the identity of this compound the reaction mixture was made alkaline by the addition of concentrated NaOH and then extracted with 3×100 ml vol. of ethyl acetate. The ethyl acetate extract was dried over anhydrous $MgSO_4$ and the solvent evaporated in vacuo to leave a small oily residue. The oil was then dissolved in a small volume of chloroform and resolved by t.l.c. on silica plates with solvent A [chloroform:methanol, 80:20 by vol] and solvent 8 [ethyl acetate:methanol:water:ammonia, 85:10:3:1 by vol]. Codeine and codeinone were used as standards to assist in the identification of the reaction products. The reaction product readily resolved into two components, with $R_f$ values of 0.41 and 0.48 in solvent A and 0.24 and 0.27 in solvent B. The compound with $R_f$ values 0.48 and 0.27 was identical with the $R_f$ value of authentic codeinone. The second compound with $R_f$ values 0.41 and 0.24 corresponds to unconverted codeine.

The compound corresponding to codeinone was purified by preparative tlc on silica plates (1000 μm, Whatman) in solvent A. The codeinone band was scraped from the plate and eluted with methanol. The methanol was removed by rotary evaporation at a temperature below 40° C. The residue was then dissolved in chloroform and the infrared spectra examined. The infra-red spectrum of the reaction product measured in chloroform exhibited an intense absorption band at 1685 $cm^{-1}$ due to a carbonyl group, which is consistent with the spectrum of authentic codeinone.

When codeine was replaced by morphine in the reaction mixture, the isolated product had $R_f$ values of 0.32 and 0.12 in solvents A and B, respectively. The proton nuclear magnetic resonance spectrum of the compound in $CDCl_3$ was also consistent with the structure of morphinone. Its principal features (relative to trimethylsilane) were as follows. A pair of doublets at 6.6δ were assigned to the aromatic AB system of the two protons on C-1 and C-2. A singlet at 4.7δ was assigned to the proton on C-5. A carbonyl group on the C-6 produces a marked change in the chemical shift of the hydrogen atoms bonded to the relevant carbon atoms (C-7 and C-8). This explains the overlapping of the multiplet at 6.6δ due to the proton at C-8, with the pair of doublets of the aromatic AB system. The signal at 6.12δ was assigned to the proton on C-7.

Non-Oxidation of Steroids by Morphine Dehydrogenase

No steroid dehydrogenase activity was detected when morphine was replaced in the standard assay with either testosterone or androsterone. No steroid dehydrogenase activity was detected when $NAD^+$ replaced $NADP^+$ in the reaction mixture.

The β-hydroxysteroid dehydrogenase from *Pseudomonas testosteroni* is the only previously described oxidoreductase enzyme to have activity against morphine, Liras et al., Applied Microbiology 30, 262–266. (1975). Unfortunately, this enzyme is disadvantageous for use in an amperometric sensor, because of its very low activity against morphine or its analogues, as indicated by the large quantities of enzyme (over 80 U/ml) required to transform codeine to codeinone. Clearly, the morphine dehydrogenase of *P. putida* M10 differs from the steroid dehydrogenase of *P. testosteroni*.

EXAMPLE 3

Example 2 was repeated, but the MDH was further purified (beyond the stages 1 to 3 shown in Example 2) and further tested.

MATERIAL AND METHODS

Further Purification of Morphine Dehydrogenase

4. FPLC Mono O chromatography

As Example 1.

5. Sephacryl S-300 gel filtration

Fractions from the Mono Q column containing the highest MDH activity were combined and concentrated to 5 ml by ultrafiltration. The concentrate was then applied to an Sephacryl S-300 column (1.5×75 cm) that had previously been equilibrated with buffer B (50 mM MOPS, pH 7.5). The flow rate was maintained at 10 ml/h and fractions of 1.5 ml were collected.

Polyacrylamide Electrophoresis (PAGE)

This was done as in Example 1.

Activity Staining

An activity stain was developed for detecting active MDH in non-denaturing polyacrylamide gels. The electrophoresed gel was incubated at room temperature in 20 ml of solution containing: 50 mM glycine-NaOH buffer, pH 10, 2 mM NADP, 0.5 mM dithiothreitol, 9 mg nitroblue tetrazolium, 0.1 mg phenazine methosulphate and 2 mM morphine or codeine.

RESULTS

In crude extracts from cells of *P. putida* M10 grown with either heroin or glucose as the sole carbon source, MDH was present at a specific activity of 0.018 unit (mg. protein)$^{-1}$. It was purified 233 fold as shown in Table 1 below:

TABLE 1

| | Purification of the MDH from P. putida M10 | | | | |
|---|---|---|---|---|---|
| Purification Step | Volume (ml) | Total Activity (units) | Total Protein (mg) | Specific activity (units. mg$^{-1}$) | Purification factor |
| Crude extract | 67 | 14 | 819 | 0.017 | 1 |
| Streptomycin sulphate | 70 | 13.3 | 806 | 0.016 | 1 |
| DEAE-Sephacel | 60 | 11.2 | 30 | 0.373 | 22 |
| Gel filtration Sephacryl S-300 | 31.5 | 8.9 | 5.1 | 1.745 | 46 |
| FPLC Mono Q | 20 | 7.03 | 1.5 | 4.700 | 274 |
| Gel filtration Sephacryl S-300 | 5 | 0.4 | 0.1 | 4.000 | 233 |

The Mono Q chromatography step produced 4 main protein peaks, the 4th peak coincident with a single peak of MDH activity. However, when the active fractions around this peak were subjected to PAGE the enzyme was found not to be homogeneous. The active fractions were, therefore, concentrated to 2 ml and reapplied to the Sephacryl S-300 gel filtration column. The pooled active fractions from this final step were >90% pure, which produced a distinct main protein band when analysed by PAGE, which coincided with a single band when either morphine or codeine were used as substrates for activity stains.

Relative Molecular Mass

The relative molecular mass of the native enzyme was determined by the previously mentioned method of Andrews from measurements on a column of Sephacryl S-200 (1.5×75 cm) calibrated with marker proteins. After the column was equilibrated with 50 mM potassium phosphate buffer, pH 7.0, a solution containing purified enzyme was applied to the bed surface and eluted with equilibration buffer at a flow of 4 ml/h, collecting 1.5 ml fractions. The elution volume of the MDH corresponded to a relative molecular mass of 32,000.

Substrate Analogues of MDH

The ability of various morphine alkaloids to serve as substrates was investigated by replacing morphine with each of the following analogues in turn: codeine, pholcodeine, morphine glucuronide, ethylmorphine, 6-acetylmorphine, heroin, thebaine, dihydrocodeine, oxycodone and codeinone. Ethanol was also tested as a substrate. Each was added at a concentration of 2 mM to a reaction mixture containing 50 mM glycine-NaOH buffer, pH 10, 5 µg of purified MDH and 2 mM NADP in a final volume of 1 ml and at 30° C. Morphine gave a specific activity of 0.002 µmol/min./mg. protein. Codeine had an activity of 1.7 times and ethyl morphine 1.2 times that of morphine. All other substrates were completely inactive. Using the more highly purified enzyme of Example 4, slightly different results were obtained. Ethanol was also tested using a concentration of MDH twenty times higher, again with a negative result. The formulae of the alkaloid substrates tested are shown below.

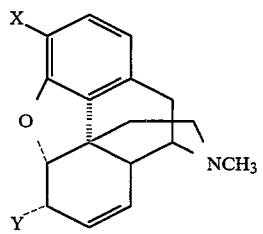

1. MORPHINE
   (X = Y = OH)

2. CODEINE
   (X = OCH$_3$, Y = OH)

3. PHOLCODEINE

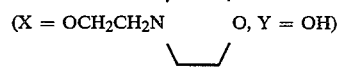

4. ETHYLMORPHINE
   (X = OC$_2$H$_5$, Y = OH)

5. HEROIN   3,6-DIACETYLMORPHINE
   (X = Y = OCOCH$_3$)

6. 6-ACETYLMORPHINE
   (X = OH, Y = OCOCH$_3$)

7. MORPHINE GLUCURONIDE

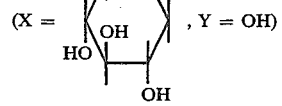

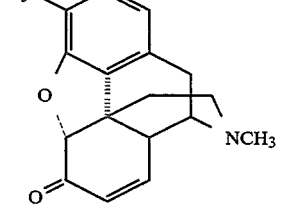

8. CODEINONE

-continued

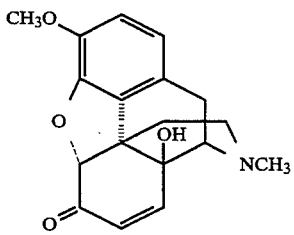

9. OXYCODONE

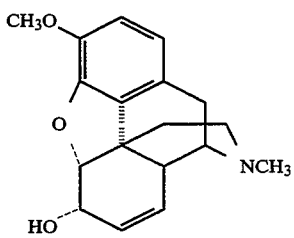

10. DIHYDROCODEINE

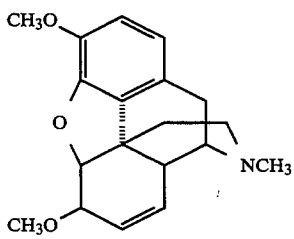

11. THEBAINE

In the reverse direction, the purified enzyme catalysed the oxidation of NADPH when codeinone was the alkaloid substrate.

Effect of Temperature

Purified MDH (48 μg) was incubated at 50° C. in 50 mM potassium phosphate buffer, pH 7.0. Activity, determined as in Example 2, was plotted against time and it was thus determined that the MDH had a half-life of 6.5 min at 50° C.

RESULTS

The MDH was purified to near electrophoretic homogeneity. Apart from morphine, only two of a wide range of analogues acted as substrates namely codeine and ethylmorphine. In this state of purity the enzyme did not show any activity towards dihydrocodeine, which differs from codeine by the absence of the double bond on the cyclohexyl ring. The enzyme showed no activity towards 6-acetylmorphine, where the hydroxyl group is on the aromatic C-3 carbon. Furthermore, with oxycodone which has a hydroxyl group at C-14 there was also no activity. Inactivity towards pholcodeine and morphine glucuronide might be due to the steric hindrance by the alkyl group at C-3, preventing the binding of the alkaloid at the active centre of the enzyme.

Furthermore, the enzyme was found to be highly specific in that it does not oxidise ethanol, a property important for use in narcotics biosensor. (Ethanol could be present from broken bottles of perfume or drink or in body fluids)

EXAMPLE 4

Alternative Preparation of Purified MDH

Bulk cultures of *P. putida* M10 (400 liters) were grown on the defined minimal medium of Example 1, supplemented with 10 mM glucose. Cells were harvested and stored at −80° C. The following procedures were performed at 4° C. and all centrifugations were run at 30,000 g for 20 min. The "Mimetic" columns were supplied by Affinity Chromatography Ltd., Freeport, Ballasalla, Isle of Man, British Isles.

(i) Preparation of Cell-Free Extract

Crude extract was prepared from 40 g (wet weight) of frozen glucose-grown cells. The cells were resuspended in buffer A (50 mM potassium phosphate-NaOH, pH 7.0, containing 1 mM dithiothreitol) at a concentration of 0.5 g (wet weight)/ml and were disrupted by 3 min ultrasonication in a Soniprep MSE Ultrasonic Disintegrator at an amplitude of 10 μm. The sonicated cell suspension was centrifuged to remove the cell debris.

(ii) Affinity chromatography on "Mimetic" Orange 3.

The cell-free extract was applied to a Mimetic Orange 3 A6XL column (2.5×5.0 cm) that had previously been equilibrated with buffer C (20 mM potassium phosphate, pH 7.0, containing 1 mM dithiothreitol). After adsorption, the column was washed extensively with buffer C containing 0.25M KCl until no further absorbance at 280 nm was evident in the eluate (approx. 500 ml), then the morphine dehydrogenase was eluted batchwise with 400 ml of buffer C, containing 0.8M KCl. Fractions (10.2 ml) were collected at a flow rate of 108 ml/h. This step separated the MDH from non-specific NADPH oxidases and removed most of the contaminating proteins.

(iii) Affinity chromatography on "Mimetic" Red 2.

Pooled fractions (54–61) from the Mimetic Orange 3 affinity chromatography step containing the highest morphine dehydrogenase activity were dialysed overnight against 2 liters of buffer C. The dialysed sample was applied to a Mimetic Red 2 A6XL column (1.0×3.0 cm) that had previously been equilibrated with buffer C. After adsorption on to the affinity matrix, the column was washed with buffer C until no absorbance at 280 nm due to protein could be detected in the eluate whence the enzyme was eluted batchwise with 0.1M KCl at a flow rate of 72 ml/h. A single peak at 280 nm was associated with all the MDH activity. The active fractions of the eluate (20–25) were pooled and concentrated in an Amicon ultrafiltration cell fitted with a YM10 membrane. SDS PAGE gave a single protein band after staining with 0.1% w/v Coomassie Blue R-250. Non-denaturing PAGE also gave a single band stained with Coomassie Blue R-250, which coincided with MDH activity, as determined by staining in a manner similar to that of Example 3.

Yields of MDH activity were improved by adding dithiothreitol to the equilibration and elution buffers.

The purification method of this Example was judged more satisfactory than those of Examples 2 and 3. The purification factor in terms of enzyme specific activity was 1216 times that of the crude extract. Accordingly some re-determinations of properties of the MDH and determinations of further properties were undertaken.

Relative Molecular Mass

The relative molecular mass of the enzyme was re-determined by the above-cited method of Andrews on columns of Sephacryl S-300 calibrated with marker proteins. After the column had been equilibrated with buffer A, a solution containing purified enzyme (3U) was applied to the bed surface of the column and eluted with equilibration buffer at a flow rate of 8 ml/h, collecting 1 ml fractions. Catalase ($M_r$ 240,000), alcohol dehydrogenase ($M_r$ 150,000) hexokinase ($M_r$ 110,000), bovine serum albumin ($M_r$ 66,000) and myoglobin ($M_r$ 17,000) were used as standards. It was determined to be 32,000±1000 as calculated from three independent determinations. When the MDH was subjected to SDS/PAGE calibrated with standard proteins, a single distinct band with an $M_r$ of 32,000±1000 was obtained, thus indicating that MDH is monomeric.

Isoelectric Point

Flat bed isoelectric focusing of the MDH was performed on an LKB Multiphor apparatus using pH 3.5–9.5 Ampholine PAG plates. A constant voltage (750 V) was applied for 5 h and the gel was maintained at 4° C. Protein was detected by staining the gel for 10 min at 60° C. with Coomassie Blue R-250 dissolved in ethanol/water/acetic acid (0.25:0.67:0.08, by vol). Gels were diffusion-destained by repeated washing in the above solvent mixture. A single isoelectric point of 4.2 was obtained.

pH Optima

MDH activity was measured by following the reduction of $NADP^+$ at 340 nm in glycine-NaOH buffer containing 3 mM morphine, 3 mM $NADP^+$ and enzyme in a final volume of 1 ml, over the pH range 7.0–10.5. In the reverse direction the reaction was measured in MOPS buffer, 0.5 mM NADPH, 1 mM codeinone and enzyme in a total volume of 1 ml, over the pH range 6.0–8.5. The unit of enzyme activity is defined as the amount of enzyme necessary to reduce 1 μmol of $NADP^+$ or to oxidise 1 μmol of NADPH per min at 30° C. The pH optima were about 9.5 and 6.5 respectively.

N-Terminal Amino Acid Determination

Automated N-terminal sequence analysis was performed on an Applied Biosystems 470A sequencer. Results are given in the Sequence Listing at the end of the description, immediately before the claims.

Stability and Thermal Inactivation

Morphine dehydrogenase was very unstable when stored at 4° C. although there was only slow loss of activity on prolonged storage (approx. 10% loss of activity over-two months) at −80° C. in buffer C. The thermal inactivation results of Example 3 were confirmed.

Kinetic Properties

Initial rates of oxidation of morphine and codeine were determined spectrophotometrically using reaction mixtures with all the components at the concentration of the standard assay (3.0 mM $NADP^+$), except for the alkaloid substrates which were varied within the range 0.15–2.0 mM for morphine, 0.015–0.5 mM for codeine and 0.5–10 mM for dihydrocodeine. Double reciprocal and Eadie-Hofstee plots were linear throughout this range, and regression analysis of the data gave apparent $K_m$ values of 0.50 mM, 0.04 mM and 2.91 mM for morphine, codeine and dihydrocodeine, respectively.

Substrate Specificity of Morphine Dehydrogenase

Dehydrogenase activity was tested using 0.35 μg of purified enzyme with the alkaloid substrates at a final concentration of 3 mM, as described for pH optima, and at pH 9.5. Alcohol substrates were at a final concentration of 50 mM, whilst D,L-mandelic acid, testosterone and androsterone were at a final concentration of 10 mM. Activities are relative to that determined with 3 mM morphine (0.0252 μmol NADPH/min=100%). Codeine had 120% activity, dihydrocodeine 7.1% and each of the following had zero activity: 6-acetylmorphine, cyclohexanol, benzyl alcohol, butan-2-ol, propan-2-ol, ethanol, propanol, testosterone, androsterone and D,L-mandelic acid.

Inhibition of MDH by Thiol-Blocking Reagents, Chelating Agents and Heavy Metals The purified MDH was incubated with the indicated reagents (a) for 10 min at room temperature and (b) for 16 h at 4° C. and then 10 min at 30° C. before enzyme activity was determined by the addition of 3 mM $NADP^+$ to the reaction mixture. The absolute activity, using 0.35 μg of enzyme, was 67 U/mg of protein (=100%). Table 2 below shows the results.

TABLE 2

Effect of various reagents on MDH activity

| Addition to the assay mixture | Conc. (mM) | (a) Relative activity (%) | (b) Relative activity (%) |
|---|---|---|---|
| None | — | 100 | 16 |
| $CuSO_4$ | 0.1 | 34 | 5 |
| p-Hydroxymercuri-benzoate (a thiol-blocking reagent) | 0.01 | 0+ | 0+ |
| N-Ethylmaleimide | 0.05 | 100 | — |
|  | 1.0 | 58 | 23* |
| Iodoacetate | 0.1 | 61 |  |
|  | 1.0 | 58 |  |
|  | 10.0 | 54 | 30* |
| EDTA | 0.5 | 104 | 18 |
| 8-Hydroxyquinoline | 0.05 | 100 |  |
| 1,10-Phenanthroline | 0.05 | 76 |  |
|  | 0.5 | 61 | 14 |
| 2,2'-Dipyridyl | 0.05 | 75 |  |
|  | 0.5 | 67 | 9 |
| Dithiothreitol | 1.0 | 97 | 64 |
| Mercaptoethanol | 1.0 | 100 | 73 |

+After incubation with 3 mM dithiothreitol for 10 min (a) 45% and (b) 23% of the activity was recovered.
*After inbucation with 3 mM dithiothreitol no further activity was recovered.

These data differentiate MDH even more clearly from most bacterial alcohol and aldehyde dehydrogenases which are insensitive to inhibition by metal chelating agents. The results suggest that a metal ion and thiol groups might be present at the active site.

EXAMPLE 5

Detection of Heroin (as the Hydrochloride) Conductimetrically

MATERIALS AND METHODS

Pharmaceutical grade heroin hydrochloride was supplied by MacFarlan Smith Ltd., (Edinburgh, Scotland). The AMCE was prepared as in Example 1.

All solutions were prepared in deionised water that had been purified with a Super Q system (Millipore, UK).

Microelectronic Conductance Electrodes Instrumentation

Microelectronic conductance devices were fabricated as described by L. D. Watson et al., Biosensors 3, 101–115 (1987/88).

These electrodes bear a gold upper layer silicon wafer supports of varying composition and finish.

The Owen bridge type circuitry used requires two pairs of well matched microconductimetric devices, wire bonded onto the same flat ceramic base support and is generally similar to that disclosed by L. D. Watson et al., supra; see also UK Patent Specification 2204408A (The Plessey Company plc).

Contacting the Microelectrodes with the Enzyme Compositions

To monitor the reaction of the AMCE with heroin hydrochloride, two 5 µl aliquots of enzyme solution in imidazole buffer (2 mM; pH 7.5) were placed on each of the reference and sample electrode pairs. Heroin hydrochloride powder (typically 2–3 grains) was dusted from a paintbrush tip onto the sample pair of electrodes to simulate pick-up of heroin. A control reaction, in the absence of AMCE, was carried out with 5 µl aliquots of imidazole-HCl buffer (2 mM; pH 7.5) on each of the reference and sample electrode pairs, followed by addition of powdered heroin hydrochloride (typically 2–3 grains) to the sample electrode.

RESULTS

The conductimetric microelectrodes, described in this section have been highly sensitive in the detection of powdered heroin hydrochloride. Addition of the powdered heroin hydrochloride to the sample cell produced a small increase in conductance measurement due to the HCl salt, but a much larger conductance increase due to AMCE degradation of the heroin to produce conducting acetate ions.

In practice, the AMCE will be incorporated in a humectant composition as described in Example 6.

EXAMPLE 6

Preparation and Use of a Humectant Composition

Preparation of a Humectant Composition

Acrylamide stock solution (A) was prepared according to methods given by Bio-rad (Richmond, Calif., U.S.A.), as follows, Acrylamide (87.6 g) and N'N'-Bismethyleneacrylamide (2.4 g) were dissolved in water in a total volume of 300 ml, filtered and stored at 4° C. in the dark. (1) Acrylamide stock solution A, (2) freshly prepared ammonium persulphate solution (10% w/v), (3) electrophoretically pure TEMED and (4) buffered AMCE from Example 1 (10 U/ml with 1 mg/ml total protein after DEAE-Sephacel chromatography in potassium phosphate buffer, 50 mM; pH 7.0) were mixed in the respective proportions of 200:10:5:1790 by vol. 10 µl of the mixture were spin-coated on to the microconductimetric electrode surface and left to gel (5–6 mins). This humectant composition has a highly stable conductance (in the absence of the dry sample) at 30° C. and its conductance is relatively little perturbed by a change in atmospheric humidity.

Testing of the Humectant Composition

Microconductimetric devices were spin coated with an AMCE/humectant mixture and stabilised by leaving them in the open atmosphere. After dusting prepared devices with heroin hydrochloride, the conductance increased rapidly and then levelled off to a constant value. Heroin hydrochloride was therefore, readily solubilised by the humectant and the consequential increase in conductance recorded was due firstly to, addition of charged species—chloride anions, protons and the quaternary ammonium cartons or secondly, as a result of AMCE activity, rapid hydrolysis of the acetyl ester groups of heroin.

EXAMPLE 7

Amperometric Detection of Heroin Using Morphine Dehydrogenase

MATERIALS AND METHODS

Morphine dehydrogenase (MDH) was isolated from *Pseudomonas putida* M10, partially purified by DEAE-Sephacel anion exchange chromatography as described in Example 2.

Using the method of B. F. Y. Yon-Hin and C. R. Lowe, Anal. Chem. 59, 2111–2115 (1987) the working electrode was prepared as strips (0.5 cm×6 cm), cut from a porous nickel sheet (40% porosity, 0.25 mm. thick, INCO Europe Ltd.) and glued with an epoxy adhesive onto a ceramic base support. All the nickel surface was insulated with epoxy resin except for two areas required for external electrical contact and for a working surface area (0.5 cm×0.5 cm). Silver/silver chloride (Ag/AgCl) reference electrodes were available from Clark Electromedical Instruments (Reading, Barks, UK). Hexacyanoferrate mediator, surface immobilised to porous nickel electrodes, was prepared as follows.

The electrodes were pretreated by first sonicating in acetone in an ultrasonic bath and subsequently drying. They were poised at a fixed potential of $-1.0$ V (vs Ag/AgCl) for 15 min; the electrodes were cycled between $-0.1$ V and $+0.4$ V until a constant background profile was observed. The hexacyanoferrate films were electrochemically grown on these electrodes from an aqueous solution containing approximately 5 mM sodium ferricyanide by sweeping continuously between $-0.1$ V and $+1.0$ V at a sweep rate of 70 mV/sec. The modified electrodes were thoroughly rinsed in distilled water. A cyclic voltammogram was thus obtained during the deposition process.

All solutions were prepared in deionised water that had been purified with a super Q system (Millipore, UK).

Steady-state current measurements were performed with the hexacyanoferrate-modified porous nickel electrode in buffer solutions (sodium phosphate (0.01M; pH 8) containing sodium perchlorate (0.1M) (3 ml) containing $NADP^+$ (2 mM) and MDH. The electrode was poised at $+0.2$ V (vs Ag/AgCl). Once a background current was obtained, an aliquot of morphine HCl (2 mM; 300 µl) was added. After the mixture was stirred briefly, the current in quiescent solution was recorded.

RESULTS

Figure 6:
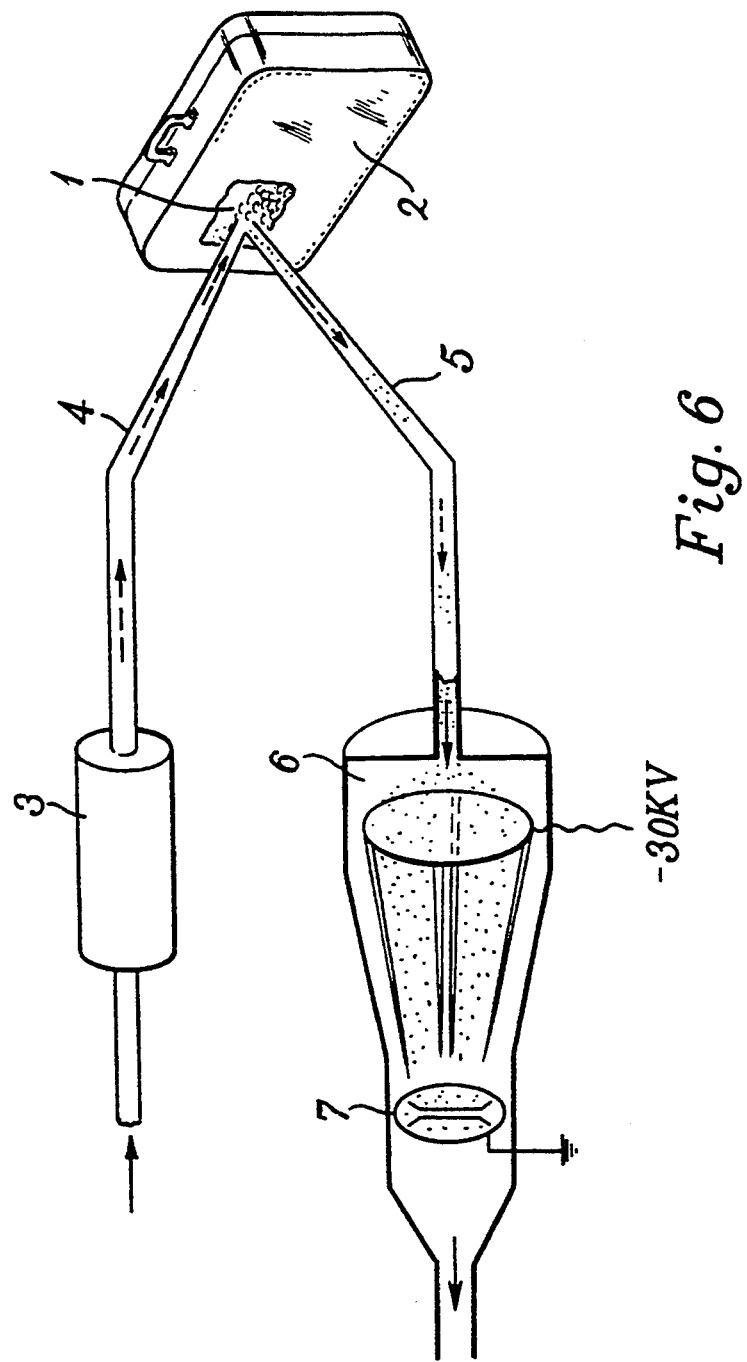
FIG. 6 is a schematic elevational view of apparatus for sampling heroin, in order to provide a sample for detection by the methods of the invention.

The steady-state current measurements recorded for morphine/MDH reaction with a nickel/hexacyanoferrate working electrode, are shown in FIG. 6.5. Following the addition of buffered solutions of morphine (1 or 2 mM), there is a rapid current increase which peaks and reduces to a steady-state value, for each drug concentration.

It is contemplated that by using a two-working electrode system it will be possible to distinguish between any current response due to morphine addition as an HCl salt and any oxidation current response due to the dehydrogenase reaction.

EXAMPLE 8

A Coupled Assay for the Detection of Heroin

Initial rates of oxidation of heroin were detected spectrophotometrically by measuring the production of NADPH, which absorbs at 340 nm, using reaction mixtures containing a final volume of 1 ml, 50 mM glycine-NaOH buffer mixture (pH 10), 2 mM NADP, 0.6 mg of partially purified AMCE, 2.8 μg of purified MDH and heroin which was varied within the range 0.25 to 1.5 mM. The effect of heroin concentration on the coupled enzyme assay is shown in Table 3 below.

mg nitroblue tetrazolium and 5 ng phenazine methosulphate. The transfer of electrons from NADPH to nitroblue tetrazolium (NBT) by phenazine methosulphate reduces NBT to the insoluble formazan, giving a blue-purple colour. This assay is very specific for heroin and very rapid, the colour developing within 30 seconds.

| Sequence listing | |
|---|---|
| SEQUENCE ID NO: | 1 |
| SEQUENCE TYPE: | Amino acid |
| SEQUENCE LENGTH: | 25 amino acids |
| FRAGMENT TYPE: | N-terminal |
| ORIGINAL SOURCE: | *Pseudomonas putida* "M10" deposited as a patent deposit as NCIMB 40119 |
| EXPERIMENTAL SOURCE: | Same as original source |
| PROPERTIES: | Dehydrogenase enzyme with high specificity for morphine |
| Ala Gly Lys Ser Pro Leu Ile Asn Leu Asn Asn Gly Val Lys Met | |
| 1           5             10               15 | |
| Pro Ala Leu Gly Leu Gly Val Phe Ala Ala | |
| 20           25 | |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
  ( A ) LENGTH: 25 amino acids
  ( B ) TYPE: amino acid
  ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
  ( A ) ORGANISM: Pseudomonas putida
  ( B ) STRAIN: m10

( x i ) SEQUENCE DESCRIPTION: SEQ ID NO:1:

Ala  Gly  Lys  Ser  Pro  Leu  Ile  Asn  Leu  Asn  Asn  Gly  Val  Lys  Met  Pro
1                      5                               10                              15

Ala  Leu  Gly  Leu  Gly  Val  Phe  Ala  Ala
                       20                             25

TABLE 3

| Heroin concentration (mM) | Activity (U × 10³) |
|---|---|
| 1.5 | 0.7 |
| 1.0 | 0.6 |
| 0.75 | 0.2 |
| 0.5 | 0.08 |
| 0.25 | 0.03 |

Activity (U) = μmol. NADPH/min.

EXAMPLE 9

A Coupled Assay for the Detection of Heroin

A colorimetric assay for the detection of heroin has also been developed, incorporating the coupled assay of Example 8. The reaction mixture contained all the components at the standard concentration (above) and heroin at 1.5 mM. Additionally, the mixture contained 0.45

We claim:

1. A process for preparing a 6-ketone from morphine or a methyl or ethyl ether thereof, which process comprises the step of oxidizing morphine or said ether in the presence of a morphine dehydrogenase enzyme and NADP+ cofactor therefor to produce said 6-ketone, said enzyme being one wherein:

(1) its first 25 amino acids from the N-terminus have sequence ID No: 1:

Ala Gly Lys Ser Pro Leu Ile Asn Leu Asn Asn Gly Val Lys Met
1           5                       10                       15

Pro Gly Leu Gly Leu Gly Val Phe Ala Ala;
        20                            25

(2) with NADP+ as cofactor it oxidizes morphine to morphinone;

(3) with the same cofactor it also oxidizes codeine and ethylmorphine but has no significant enzymatic action on heroin, 6-acetylmorphine, thebaine, oxycodone, morphine glucuronide pholcodeine or ethanol;

(4) its molecular weight is about 32,000 Daltons, as determined by gel filtration; and (5) in glycine-NaOH buffer it exhibits optimal reactivity with morphine at pH about 9.5; and its isoelectric point, determined by flat bed isoelectric focussing in a gel, is 4.2.

2. A process according to claim 1, wherein the oxidation is carried out in air at a temperature of from 25° to 35° C.

* * * * *